(12) United States Patent
Baur et al.

(10) Patent No.: US 10,094,651 B2
(45) Date of Patent: Oct. 9, 2018

(54) POSITIONING SYSTEM AND METHOD (71) Applicant: CSEM Centre Suisse d'Electronique et de Microtechnique SA-Recherche et Développement, Neuchâtel (CH)

(72) Inventors: Charles Baur, St-Aubin-Sauges (CH); Amina Chebira, Lausanne (CH); Edoardo Franzi, Cheseaux-Noréaz (CH); Eric Grenet, Neuchâtel (CH); David Hasler, Neuchâtel (CH)

(73) Assignee: CSEM CENTRE SUISSE D'ELECTRONIQUE ET DE MICROTECHNIQUE SA—RECHERCHE ET DÉVELOPPEMENT, Neuchatel (CH)

( * ) Notice: Subject to any disclaimer, the term of this patent is extended or adjusted under 35 U.S.C. 154(b) by 114 days.

(21) Appl. No.: 14/995,739

(22) Filed: Jan. 14, 2016

(65) Prior Publication Data
US 2016/0209203 A1    Jul. 21, 2016

Related U.S. Application Data

(63) Continuation-in-part of application No. 14/597,434, filed on Jan. 15, 2015, now Pat. No. 9,696,185.

(30) Foreign Application Priority Data

Jan. 15, 2015   (EP) .................................... 15151233

(51) Int. Cl.
| *G01B 11/00* | (2006.01) |
| *A61B 90/30* | (2016.01) |
| *G01S 5/16* | (2006.01) |

(52) U.S. Cl.
CPC ............ *G01B 11/002* (2013.01); *A61B 90/30* (2016.02); *G01S 5/163* (2013.01); *A61B 2090/309* (2016.02)

(58) Field of Classification Search
CPC ................. G01B 11/002; A61B 90/30; A61B 2034/2046
See application file for complete search history.

(56) References Cited

U.S. PATENT DOCUMENTS 6,141,104 A * 10/2000 Schulz ..................... G01D 5/34
356/616
6,417,836 B1   7/2002 Kumar et al.
(Continued)

FOREIGN PATENT DOCUMENTS

WO            12007561 A2    1/2012

OTHER PUBLICATIONS

R. Hartley and A. Zisserman, Multiple view geometry in computer vision, second edition, Cambridge university press, ISBN 0521 54051.

(Continued)

*Primary Examiner* — Tony Ko
(74) *Attorney, Agent, or Firm* — Pearne & Gordon LLP (57) ABSTRACT

A positioning system, in particular, six-dimensions positioning system of a shadow sensor with respect to a constellation of light sources is provided. The sensor can be a shadow sensor and has a mask and a 2D imager. By recording the shadow of the mask cast by each light source on the imager, and by properly multiplexing the light sources, the system can compute the 6D position of the shadow sensor with respect to the constellation of light sources. This computation is based, in part, on treating the shadow of the mask cast on the imager as the equivalent of the projection of light in a pinhole or projective camera. In one embodiment, the system is applied in a surgical domain. In another embodiment, the system is rapidly deployed.

13 Claims, 6 Drawing Sheets

(56) References Cited

U.S. PATENT DOCUMENTS

| | | |
|---|---|---|
| 6,978,167 B2 | 12/2005 | Dekel et al. |
| 7,768,498 B2 | 8/2010 | Wey |
| 7,876,942 B2 | 1/2011 | Gilboa |
| 8,368,647 B2 | 2/2013 | Lin |
| 8,885,177 B2 | 11/2014 | Ben-Yishai et al. |
| 2013/0106833 A1 | 5/2013 | Fun |
| 2013/0120763 A1* | 5/2013 | Grenet .................. G01C 3/085 |
| | | 356/615 |

OTHER PUBLICATIONS

Haralick, Bert M., Chung-Nan Lee, Karsten Ottenberg, and Michael Nölle. "Review and Analysis of Solutions of the Three Point Perspective Pose Estimation Problem." International Journal of Computer Vision 13, No. 3 (1994): 331-56.

A. Chebira, E. Grenet, P-A. Beuchat, A. Corbaz, E. Franzi, D. Hasler, and P. Masa. "Nanotracking for image-guided microsurgery", Swiss Center for Electronics and Microtechnology (CSEM), Neuchâtel, Switzerland, HearRestore, RTD 2013.

* cited by examiner

POSITIONING SYSTEM AND METHOD

REFERENCE DATA

This application claims the priority of 15.01.2015 of the US patent application having U.S. application number Ser. No. 14/597,434 and the priority of 15.01.2015 of the EP patent application having application number EP20150151233, the contents whereof are hereby incorporated.

FIELD OF THE INVENTION

The present invention concerns a system and method for positioning a sensor with respect to a plurality of light sources. In particular, the present invention concerns a system and method for six-dimensional (6D) positioning a sensor with respect to a plurality of light sources.

DESCRIPTION OF RELATED ART

In traditional three to six dimensional positioning systems, a camera records the position of a set of points in the scene. These points can appear in the form of a predefined shape, e.g. a cross or a small ball whose center is computed using conventional image processing techniques. In general a target, i.e. a body, in particular a rigid body comprises these points. Other known systems use point light sources instead of objects with a predefined shape, which makes the detection easier.

The camera of those known positioning systems is a large camera or a stereo-camera system. In this context, a camera is "large" if its smallest dimension is few cm long, e.g. 5 cm long, and its largest dimension is higher than 15 cm, e.g. 1 m or more.

The interesting information is the motion of the target comprising the set of the above-mentioned points, in particular the position of the target with respect to a "world" or reference coordinate system. The camera is in general fixed. In this context, a camera is "fixed" if it is attached to the reference coordinate system, thus it has a known 6D position in the reference coordinate system. This does not necessarily mean that the camera does not move, it could be displaced, as long as this displacement is accounted for by computing the reference coordinate system of the target.

The document U.S. Pat. No. 6,417,836 (Lucent Technologies) discloses a method to track an object in 6D using a camera and a set of five LEDs disposed on a planar surface. Five LEDs are necessary because the LEDs are taken in a single shot by the camera and the identity of each LED is determined thanks to the geometrical configuration of the five LEDs, which allows to compute a value which is invariant to projective transformations. This value is a function of a set of points associated with the planar surface, each corresponding to one of the light sources, with a given one of the points selected as a principal point.

The document WO 2012/007561 filed by the applicant discloses a system that computes the azimuth and elevation of a light source with respect to a sensor with very high precision. It also discloses the method to compute the 3D position of the light sources using several of these sensors.

The document U.S. Pat. No. 8,368,647 discloses various methods for multiplexing the signal from different point light sources in time, to be recorded by a CCD camera.

The document US 2013/0106833 (FUN) describes the use of conventional imaging to track an object in 6D. It discloses a tracking system that makes use of a single camera and complex markers. The markers are designed so as to get a good tracking accuracy on an image. A similar system is disclosed in documents U.S. Pat. No. 7,768,498, U.S. Pat. No. 6,978,167 and U.S. Pat. No. 7,876,942.

An aim of the present invention is to propose a positioning system and method alternative to the known solutions.

Another aim of the present invention is to propose a positioning system and method obviating or mitigating one or more disadvantages of the known solutions.

Another aim of the present invention is to propose a positioning system allowing the positioning of a sensor with regard to a plurality light sources.

Another aim of the present invention is to propose a positioning system devoid of cameras.

Another aim of the present invention is to propose a positioning system more compact than known solutions.

Another aim of the present invention is to propose a positioning system and method more precise than known solutions.

Another aim of the present invention is to propose a positioning system and method which can be efficiently used in a surgical environment.

Another aim of the present invention is to propose a positioning system which can be rapidly deployed.

Another aim of the present invention is to propose a positioning system allowing to compute the position arbitrary number of sensors in the scene, once the light source configuration is setup.

BRIEF SUMMARY OF THE INVENTION

According to the invention, these aims are achieved by means of a positioning system, in particular a six dimensional (6D) positioning system, comprising:
  a plurality of light sources;
  at least one shadow sensor configured to sense shadows cast on the shadow sensor by light emitted from the light sources;
  a processor.

In one preferred embodiment, the light source according to the invention is a punctual light source, i.e. it can be approximated as a mathematical point. The light source according to the invention comprises in general integrated optical components. In one preferred embodiment, the dimension of the light source without considering those optical components is less than 5 mm, preferably less than 1 mm. A non-limitative example of a light source according to the invention is a LED.

According to one preferred embodiment, the shadow sensor is the sensor as described in WO 2012/007561, the entirety of which is incorporate herein by reference. In one preferred embodiment, it comprises a mask and an imager, the mask having repetitive elements and a distinctive element: as the light from the light sources of the target passes through the mask, a shadow of the mask is cast on the imager. Each repetition of the elements contributes to the precision of the measurement. Preferably, the mask is parallel to the imager. In one preferred embodiment, the shadow sensor comprises at least three repetitive elements in one direction and at least three repetitive elements in another different direction.

According to the invention, the maximum distance between any light sources according to the invention is larger than fifty times a width and/or a height of an imager of the shadow sensor. Typically, the distance between the most separated LEDs are in the order of 50, 100 or even 1000 times larger than the size of the imager (width or height, whichever bigger) in the shadow sensor. For example, if the shadow sensor is 5 mm wide, then the size of the LED structure will likely be larger than 50 cm wide, in the average in the order of 1.5 m wide. In one preferred embodiment, the light sources are tiny and/or can be made invisible.

The processor according to the invention is configured to:
sync the shadow sensing with the pulsing of the light sources;
distinguish between the sensed shadows from each of the light sources of the target;
determine two-dimensional (2D) positions corresponding to each of the light sources of the target based on the sensed shadows; and
compute the 6D position of the at least one shadow sensor with respect to the light sources based on the determined 2D positions.

The system according to the invention reverses the traditional paradigm of 3D to 6D computation. Here, the position of interest is the position of at least one shadow sensor, and the reference coordinate is made of a plurality or constellation of light sources.

The processor is configured to compute its position with respect to the plurality of light sources. In one preferred embodiment, it is configured to send this information to whatever equipment that needs it. This shift of paradigm relies on the shadow sensor, which can be made small, light and low power. Using today's technology, without battery, a shadow sensor can be made as small as 3×3×1 mm.

One major advantage of the system according to the invention is its compactness. Geometrically, the more compact the equipment, the less accurate. The system according to the invention takes advantage of two phenomena:

First, the light sources are set far apart, resulting in the equivalent of a non-compact system in terms of accuracy, despite the compactness of the shadow sensor. If the light sources are set apart from a few meters, the lever arm is huge. The lever arm determines the precision of the positioning: the higher the lever arm, the more precise the positioning.

Second, the shadow sensor measurements are very precise, much more precise than the identification of a target point/object in the scene seen by a conventional camera in the known positioning systems. Thus, if compared to a known system where one would put a camera at the light location—set far apart—and several targets at shadow sensor location, one would not even get close to obtaining the same precision. Indeed, right now, the position of the shadow can be computed with a precision of the order of 1 nm (or even below in some situations), whereas the location of a target seen by a high-resolution camera will hardly exceed a precision of 100 μm.

In one embodiment, the processor is located inside the shadow sensor, and it is configured to compute the two dimensional positions (x-y) of each light source only, and send them to another different and preferably external processor which computes the 6D position of the shadow sensor(s) with respect to the plurality of light sources based on the two-dimensional positions. In another embodiment, the processor located inside each shadow sensor is configured to compute the two-dimensional positions (x-y) of each light source, as long as the 6D position of the shadow sensor(s) with respect to the plurality of light sources.

In one embodiment, the positioning system according to the invention comprises several shadow sensors. In this embodiment, a processor (in at least one shadow sensor or in each shadow sensor or an external processor) is configured to compute the 6D position of those shadow sensors.

In one preferred embodiment, the system according to the invention comprises:
three or more light sources;
an assembly comprising two shadow sensors with known relative position.

In this embodiment, the processor is configured to compute the 6D position of the assembly with respect to the three or more light sources. In one preferred embodiment, the two shadow sensors are synchronised, i.e. they are configured so as to sense the shadow according to a common exposition schedule (or shadow sensing).

In one embodiment, the processor is configured to distinguish between the sensed light from each of the light sources based at least in part on temporal modulation of the light sources.

In another embodiment, each shadow sensor further comprises a photodiode for syncing the shadow sensing with the pulsing of the light sources and/or for identifying which light source is emitting light.

In one preferred embodiment, the 6D position of the shadow sensor(s) is computed by considering each shadow sensor as a pinhole camera. This allows to use projective geometry computations. The applicant discovered that surprisingly, from a geometry computation point of view, the shadow sensor can be considered as a pinhole camera, although the shadow sensor according to the invention does not allow to record the image of the scene as a camera. Moreover, the shadow sensor according to the invention works with a single light source at time.

It should be noted that—from a geometry computation point of view, and depending on how the coordinates of the shadow sensor are computed—each shadow sensor can be considered not only as a pinhole camera, but also as a projective camera. In the literature, a pinhole camera indicates a camera made of a box with a single small aperture (the pinhole) wherein light from a scene passes through this aperture and projects an image on the opposite side of the box. In this context, however, the expression "pinhole camera" is slightly more generic: it indicates a camera whose projection properties can be modelled as a linear system in projective space. In other words, the output of the camera needs not to be inverted with respect to the scene. Moreover, the camera needs not to have an isotropic coordinate system to express a 2D position to be called a "pinhole camera". In the literature, these cameras are either called "pinhole cameras" or "projective cameras": Therefore in the present context the expressions "pinhole cameras" and "projective cameras" are synonyms. In other words, in this context, the expression "pinhole camera" indicates also a "projective camera", as the output of the camera needs not to be inverted with respect to the scene. In practice, it means that the shadow sensor can be represented in 3D by a four by four matrix, giving more flexibility to the representation of the position of the shadow computed by the processor.

It should also be noted that, when talking into account non-linear effects inside the shadow sensor, i.e. effects that deviate from an ideal pinhole or projective camera such as the refraction described later in the text, the non-linear effect is used to estimate the position of the shadow in the best possible way, and then, is discounted for. In other words, once the non-linear effect is estimated, the position of the shadow is corrected to as to correspond to the position obtained by an ideal pinhole or projective camera prior to apply the well known six dimensional projective geometry computation.

In one preferred embodiment, the system according to the invention comprises a number of light sources is equal or higher than four.

In another embodiment, at least four light sources are coplanar, i.e. they are placed on the same plane. This embodiment allows to use linear computation method for determining the two dimensional (2D) positions corresponding to each of the light sources based on the sensed shadows.

In one preferred embodiment, the system according to the invention comprises at least a surgical tool and a surgical lamp, at least one shadow sensor being placed on a surgical tool and all the light sources whose sensed shadows are used by the processor in the 6D computation being placed in or on the surgical lamp.

In one embodiment, the light sources are positioned at fixed relative locations within or on the surgical lamp.

In one embodiment, the surgical lamp comprises at least one additional light source emitting in the visible part of the light spectrum and each light source is configured to emit light not interfering with the light of the surgical lamp, e.g. to emit infrared light.

In one embodiment, the light sources are connected and a radio link is used to sync the shadow sensor.

According to another different embodiment, the system according to the invention comprises a set of at least two light source modules, each light source module comprising:
  a light source;
  communication means for communicating with other light source modules;
  a clock;
  fixation means for fixing the piece on a support, e.g. a wall, a ceiling, a furniture, the fixation means comprising e.g. a magnet.

In one embodiment, the system according to the invention comprises a battery and RF communication means.

In this embodiment, the system comprises a wired network connecting all the light sources whose sensed shadows are used by the processor in the 6D computation, to the battery and RF communication means.

In one preferred embodiment, one light source module acts as a master, at least some other light source modules act as slaves. In this embodiment, the light source module acting as a master comprises the above-mentioned battery and/or RF communication means.

In another embodiment, each light source module comprising a battery and RF communication means.

In another embodiment, each light source module comprising an RF communication means and a wired connection to an external power source.

The present invention concerns also a method for estimating a position, in particular a six dimensional (6D) position, of a shadow sensor with respect to a plurality of light sources, the shadow sensor being configured to sense shadows cast on the shadow sensor by light emitted from the light sources, the maximum distance between any of the light sources being larger than fifty times a width or a height of an imager of the shadow sensor, the method comprising;
  sync a shadow sensing with a pulsing of the light sources;
  distinguish between the sensed shadows from each of the light sources;
  determine two dimensional (2D) positions corresponding to each of the light sources based on the sensed shadows; and
  compute a 6D position of the at least one shadow sensor with respect to the light sources based on the determined 2D positions.

In one embodiment, the method according to the invention comprises the following steps:
  tracking the position of the shadow sensor;
  rendering this tracking in a CAD design.

According to a possible independent aspect of the invention, which can be combined also with the previous aspects of the invention, the present invention concerns also a method for estimating the three dimensional (3D) relative position of a plurality of light sources, using an assembly comprising at least two shadow sensors with known relative positions, the shadow sensors being configured to sense shadows cast on the shadow sensors by light emitted from the light sources, the method comprising;
  record a projection of at least three points from a fixed location, each point corresponding to the (3D) position in space of a light source, a projection of a point being recorded as the two dimensional (2D) positions of the sensed shadows cast by this light source on each shadow sensor of this assembly;
  compute the three dimensional position of each point with respect to this fixed location;
  repeat this recording and computing steps from a different fixed location, so as to obtain M recordings comprising each the projection of a set of the same Q light sources, M and Q satisfying a predetermined constraint;
  compute the position of every light source within a common reference frame.

According to a possible independent aspect of the invention, the method according to the invention comprises also the following steps:
  sense shadows cast on an assembly comprising at least two shadow sensors with known relative positions, by light emitted from the light sources,
  record a projection of at least three points from a fixed location, each point corresponding to the position in space of a light source, a projection of a point being recorded as the two dimensional positions of the sensed shadows cast by said light source on each shadow sensor of said assembly;
  compute the three dimensional position of each point with respect to said fixed location;
  repeat said recording and computing steps from a different fixed location, so as to obtain M recordings comprising each the projection of a set of the same Q light sources, M and Q being integer numbers satisfying a predetermined constraint;
  estimate the three dimensional relative position of every light source (200) within a common reference frame.

According to another possible independent aspect of the invention, which can be combined also with the previous aspects of the invention, the present invention concerns also a method for estimating the three dimensional (3D) relative position of a plurality of light sources, using a shadow sensor configured to sense shadows cast on the shadow sensor by light emitted from the light sources, wherein at least two light sources are at a fixed position with respect to each other, the method comprising;
  record a projection of at least six points from a fixed location, each point corresponding to the (3D) position in space of a light source, a projection of a point being recorded as the two dimensional (2D) position of the sensed shadow cast by this light source on this shadow sensor;
  repeat the recording and computing steps from a different fixed location, so as to obtain N recordings comprising each the projection of a set of the same P light sources, N and P satisfying a predetermined constraint;

compute the position of every light source within a common reference frame, the positions being defined up to a scale factor;

scale every computed position so that the computed relative location of the at least two light sources with known relative positions matches the known relative positions.

According to a possible independent aspect of the invention, the method according to the invention comprises also the following steps:

sense shadows cast on the shadow sensor by light emitted from the light sources, wherein at least two light sources are at a fixed position with respect to each other;

record a projection of at least six points from a fixed location, each point corresponding to the position in space of a light source, a projection of a point being recorded as the two dimensional position of the sensed shadow cast by said light source on said shadow sensor;

repeat said recording and computing steps from a different fixed location, so as to obtain N recordings comprising each the projection of a set of the same P light sources, N and P being integer numbers satisfying a predetermined constraint;

compute the three dimensional relative position of every light source within a common reference frame, said position being defined up to a scale factor;

scale every computed three dimensional relative position so that the computed three dimensional relative position of said at least two light sources matches said known fixed position.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENT(S) OF THE INVENTION

Figure 1A:
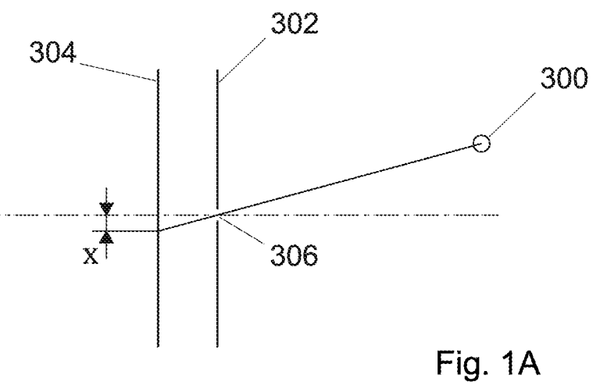
FIG. 1A shows a section view of a pinhole camera and an object point.
Figure 1B:
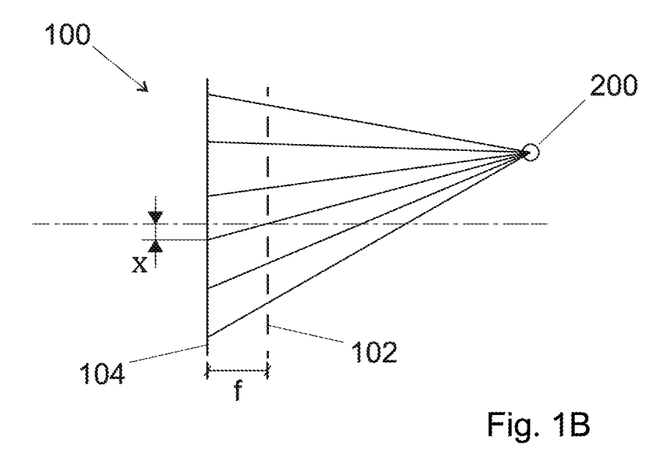
FIG. 1B shows a section view of a shadow sensor and of a light source of the system according to the invention.

FIG. 1B shows a section view of a shadow sensor 100 and of a light source 200 of the system according to the invention. Only one light source 200 is illustrated for clarity purposes. However, it must be understood that the system according to the invention comprises a plurality of light sources, which are multiplexed in time or which emit at different wavelengths, as will be discussed.

In one preferred embodiment, the system according to the invention comprises more than one shadow sensor 100.

Each shadow sensor 100 is configured to sense shadows cast on the shadow sensor by light emitted from the light source 200.

According to one preferred embodiment, the shadow sensor 100 is the sensor as described in WO 2012/007561, the entirety of which is incorporate herein by reference. In this embodiment, it comprises a mask 102 and an imager 104, the mask 102 having repetitive elements and a distinctive element: as the light from the light source 200 passes through the mask 102, a shadow of the mask 102 is cast on the imager 104. Each repetition of the elements contributes to the precision of the measurement. Preferably, the mask 102 is parallel to the imager 104. In one preferred embodiment, the mask 102 of the shadow sensor 100 comprises at least three repetitive elements in one direction and at least three repetitive elements in another different direction.

In one preferred embodiment, the 6D position of the shadow sensor(s) is computed by considering each shadow sensor as a pinhole camera, so as to use projective geometry computations. FIG. 1A shows a section view of a pinhole camera 302 and an object point 300. The light from the scene comprising the object point 300 passes through the pinhole 306.

The applicant discovered that surprisingly, from a geometry computation point of view, the shadow sensor 100 can be considered as a pinhole camera, or as a projective camera.

The position x is computed from the shadow of the mask 102 (FIG. 1B) and it is the same as the projection of the object point 300 of the image plane 304 of the pinhole camera of FIG. 1A. In FIGS. 1A and 1B, x is a two-dimensional variable, although shown in 1D for clarity purposes. The focal length f of the shadow sensor 100 is the distance between the mask 102 and the image plane 104. In the shadow sensor 100, the z distance from the mask 102 to the light source 200 (measured along the optical axis) could be obtained by computing the scale of the shadow of the mask 102: if the shadow is of the same scale than the mask 102, then the light source 200 is very far away, if it is larger than the light source 200, it is close to the mask 102. By computing the enlargement ratio, it is possible to determine this z distance.

In practice, however, this measurement is not very well conditioned, and thus results in a measurement with poor precision. In substance, the estimation of position x is about 100 times more precise than the estimation of the z distance.

Because of the poor performance in the z estimation, in one preferred embodiment the method performs an estimation of the position of the shadow sensor using only the 2D position (i.e. x) estimation for each light source 200.

According to known geometric rules, the projection of four light sources 200 is used to compute the 6D position of the sensor 100 with respect to the light sources 200, provided that the relative position of the light sources are known.

There are efficient linear techniques to compute the 6D position on the basis of the x position, which do not deliver the optimal result in terms of accuracy, and there are non-linear techniques that deliver better accuracy but they are iterative, and need an initial position estimate. The initial position estimate of the iterative methods can be given by a linear technique, by a tracking process over time, or set to an initial arbitrary value.

For example, the computation of the 6D position of a plane in space using four or more correspondences ($\{x_i \leftrightarrow x_i'\}$, as discussed above can be determined according to multiple view geometry principles. This computation can be applied to a scenario where the light sources 200 are all on the same plane. To do so, first the 2D homography matrix between the sensor plane and the light source plane is computed, such that $$x_i' = H x_i \quad (1)$$

where H represents a 2D homography matrix.

Then, the first two columns of a rotation matrix and a translation vector can be retrieved according to the relationship:

$$H = K[r_1, r_2, t] \quad (2)$$

where K are internal parameters, $r_1$ and $r_2$ represent the first two columns of the rotation matrix, respectively and t represents the translation vector.

From this information, the full 6D transformation from the sensor plane to the light source plane (provided that the "world" origin is located on the shadow sensor) can be obtained using the focal length f of the shadow sensor.

The document R. Hartley and A. Zisserman, *Multiple view geometry in computer vision*, second edition, Cambridge University Press, the entirety of which is incorporate herein by reference, describes in the algorithm 4.2 the method for computing the 2D homography between the camera plane and the light source plane. Its equation 8.1 allows to retrieve the first two columns of the rotation matrix and the translation vector.

Figure 2:
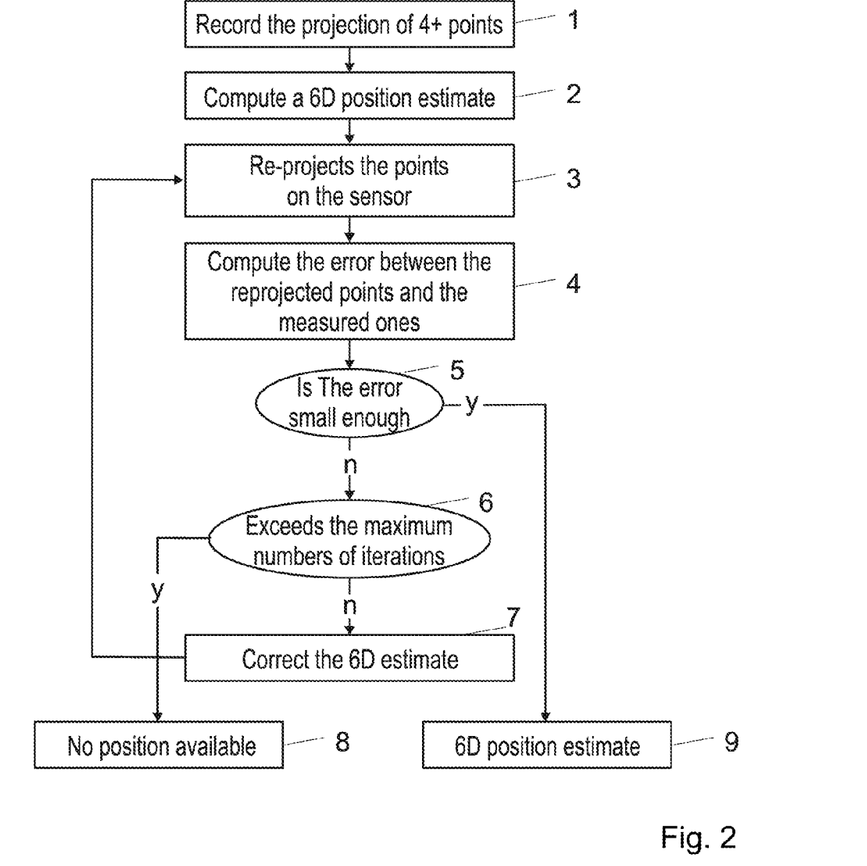
FIG. 2 shows a flow chart of some steps of the method for computing the 6D position of a shadow sensor with respect to a plurality of light sources according to one embodiment of the invention.

FIG. 2 illustrates a flow chart of the 6D position computation. A computing module, for example a computing module controlled by a processor, starts in step 1 by recording the projection of four or more points. In this context, a "point" indicates the location of a light source in the space.

The number of "points", as the term is used herein can generally be understood as the sum of the number of light sources that the sensors in the system can record. When a single shadow sensor is used, any point generates a measurement consisting of two coordinates. When an assembly of two sensors is used, any point generates a measurement consisting of four coordinates. For example, a system with four light sources and one sensor has four points, which represent eight coordinates; a system with three light sources and two sensors has three points, which represent twelve coordinates. In other words, the projection of a light source on a sensor system can be understood to be a "point".

However it should also be noted that in some conditions, e.g. when there is a-priori knowledge on the constellation of light sources position or when the point coordinate (the two-dimensional x) is not the only information retrieved from each light source, it is possible to use fewer than four points to compute the 6D position, as will be discussed.

Then, in step 2, the system computes a first estimate of the 6D position, either using past information (tracking) or using any suitable computation method, for example the linear method described above.

In the step 3, from the 6D estimate, the system virtually reprojects the points on the sensor 100, using the pinhole model.

In step 4, an error value is computed by comparing the reprojected 2D position of every light source 200 with the 2D position computed using the shadow. In some embodiments, the error value may be computed using an error metric such as a weighted L1 norm, but any suitable error metric could be used. Since the problem is over-constrained, the error is not null.

Thus, in step 5, an iterative error minimization can be performed in order to improve the 6D position estimate. To compute the L1 weighted error norm, the weight can be set using the contrast of the shadow. In other words, the more contrasted the shadow, the more "visible" the light source 100, the more confidence in the measurement and the higher the weight.

If the error is small enough, then the system computes the 6D position estimate of the shadow sensor 100 with respect to the plurality of light sources 100 (step 9). For example, a small enough error may correspond to an error generated when the reprojected points are less than a quarter pixel away from the measured points on average. As an alternative, the "small enough" error can be characterised for a given application, with a given sensor type and dimension, and a given target type and dimension, in a calibration phase by measuring the standard deviation of the measured re-projection error on a set of measurement whose 6D position estimation is known to be correct; the small enough error threshold can be set to, for example, three times said standard deviation.

If the error is not small enough, then in step 6 the system check if the number of iterations exceeds a threshold: if so, then the system declares that no position is available (step 8). If number of iterations does not exceed this threshold, then the system corrects in step 7 the 6D position estimate. The value of this threshold depends principally depends on the mathematical method used in the computation. In one preferred embodiment, the value of this threshold is about 20.

In the iterative process of FIG. 2, the estimate of the shadow position from the shadow signal can be updated as well so as to better correspond to the pinhole model or to the projective model. For example, by having an estimate of a light source's 3D location, the assumed shape of the shadow can be computed by accounting for scaling and/or refraction. A shifted version of this assumed shape can be used to estimate the shadow position.

In a preferred embodiment, the mask 102 of the shadow sensor 100 is composed of repetitive patterns and of a distinctive element, for example, a form of a grating. In this way, as light from the light source 200 passes through the mask 102, a distinct shadow pattern is cast on the imager 104 behind the mask 102 in accordance with the position of the sensor 100 with respect to the light source 200 and the pattern of the mask 102.

By using a repetitive pattern for the mask 102, the precision of the sensor 100 may be increased by improving the measurement of the sensed pattern. By recording the shadow of the mask 102 cast by each light source 200 on the imager 104, and by properly multiplexing the light sources 200, the system can compute the 6D position of the shadow sensor 100 with respect to the plurality of light sources 200.

In one preferred embodiment, the repetitive pattern of the mask 102 may be a checkerboard engraved on piece of glass. In another embodiments, the repetitive pattern may be realized by using a set of micro-lenses. In one preferred embodiment, the repetitive pattern of the mask 102 is a regular pattern, wherein a shape is repeated at regular intervals on the mask 102.

Ideally, a mask should cast a shadow made of regular alternations of shadow and light.

Figure 3:
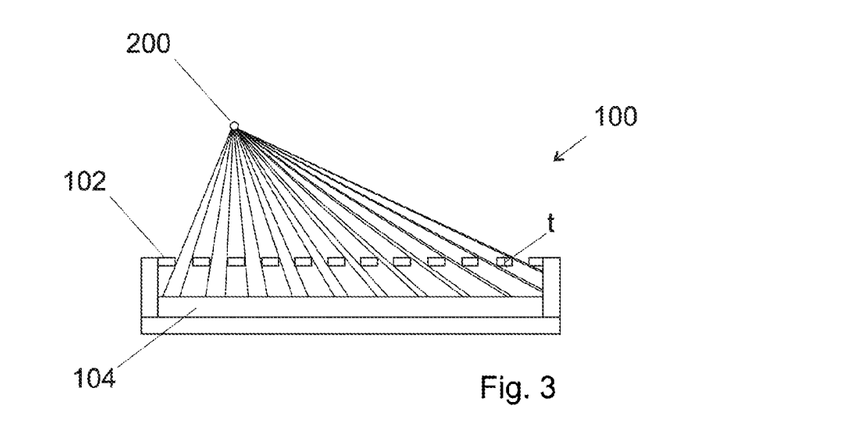
FIG. 3 shows a section view of a light source and of a shadow sensor of the system according to one embodiment of the invention.

In practice, if looked at in a small scale, a regular mask does not generate a strictly regular shadow. This is because the mask 102 has a certain thickness t (as illustrated in FIG. 3), because of refraction effects on the glass of the mask 102, and/or because of other optical phenomena.

Nevertheless, the mask 102 should generate an approximate regular pattern, such that, in the first step of the computation of FIG. 2, it is possible to assume a regular pattern and apply an efficient and accurate algorithm to compute the position estimate.

In one embodiment, the size of the imager 104 is few mm, the mask 102 to imager 104 distance is about 0.3 mm to 2 mm, e.g. 0.5 mm to 1 mm, and the distance between two repetitive patterns on the mask 102 is about 100 µm. Thus, the size of a shadow sensor 100 is about 10 mm×10 mm×2 mm, e.g. including various processors and other components, but excluding a battery. In other embodiments, the size of the shadow sensor 100 is about 4 mm×4 mm×1 mm, or even 3 mm×3 mm×1 mm. However, it should be noted that these dimensions are not intended to be limiting and even smaller shadow sensors are envisioned to be within the scope of the present disclosure. Moreover, the shadow sensor does not necessarily have a squared section. The main advantage of the shadow sensor in terms of size, compared to a traditional camera, is its thickness: the mask-imager assembly being much thinner than a lens-imager assembly of a standard camera.

The shadow computation works in principle as described in equation 2 of WO 2012/007561, reproduced herein:

$$\begin{cases} A = \sum_x \sin\left[\frac{2\pi}{\Delta P} M \cdot x\right] \cdot s(x) \\ B = \sum_x \cos\left[\frac{2\pi}{\Delta P} M \cdot x\right] \cdot s(x) \\ dX = -\text{atan2}(A, B) \cdot \Delta P \end{cases} \quad (3)$$

where M is the pixel pitch, s(x) is the shadow pattern, x is the pixel coordinate, and a tan 2(A,B) is the arctan(A/B) function defined in [−π, π]. In sum, the above equation uses the shadow image to take the sum over the lines and the sum over the columns, resulting in two signals. One signal is used to estimate the x coordinate (in this case, a mono-dimensional coordinate), the other to estimate the y coordinate.

To take advantage of the repetition of the pattern present in the mask 102, it is assumed that the shadow has a given shape, the measured shape is correlated with shifted versions of the assumed shape. The dot product could also be used instead of a correlation. However, it should be noted that it is preferred to use the same metric throughout the computation.

In WO 2012/007561, the assumed shape is a sinusoid and two versions of the assumed shadow shape shifted by half the shape period are used. The ratio of the two dot products is taken, which follows an arctan law, to retrieve the position.

More generally, when starting with a position estimate, a three shifted version of the assumed shape can be used, making sure that among the versions, the first is shifted too far in one direction and the last is shifted too far in the opposed direction. Then, a correlation (or dot product, or any similarity metric) value for each can be calculated and a parabola can be fit to the three values. The position of the parabola extremum gives the position estimate of the shadow. In other words, it can be assumed that the similarity metric can be well approximated by a quadratic rule with the shift.

When using a more complex optical model, for example by taking into account the refraction phenomenon, the shifting of the shadow assumed shape is computed by virtually shifting the light sources 200 and computing the resulting shadow according to the refraction model.

To measure the actual shape of the mask 102, a shadow recording can be taken by exposing the shadow sensor 100 to a collimated light source, where the rays of the collimated light source are parallel to the optical axis of the sensor 100. This shape can then be used to compute the shape of the shadow by assuming a 3D position of the light source 200 in the context of an iterative position computation process.

While the above described procedure gives the position up to an undetermined multiple of the signal period, the absolute shadow location can be computed by using a distinctive element, as described in WO 2012/007561. For example, the distinctive element can be a 2D code interlaced with the repetitive patterns. It can also be a set of missing repetitive elements, for example defining a crosshair in the middle of the mask. The missing element creates a sort of "hole" in the repetitive pattern, the hole being not a physical hole, it represents rather the absence of a repetitive element. It must be understood that the missing repetitive elements are not necessarily repetitive. The missing elements can also be set on the border, thus having a pattern of repetitive elements that do not cover completely the imager of the sensor. The preferred solution uses a set of missing (repetitive) elements.

Figure 4:
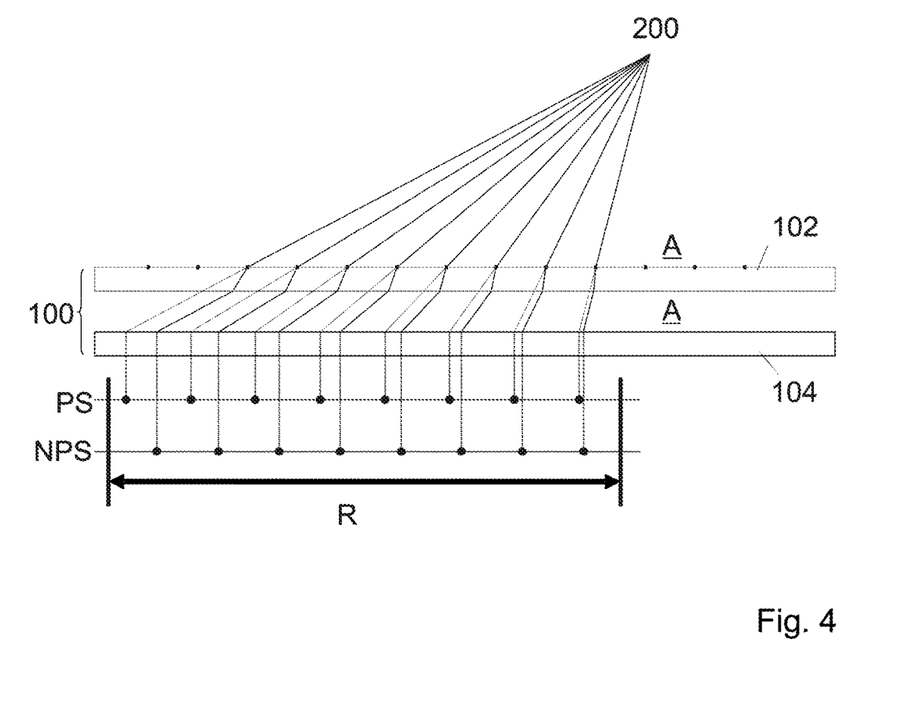
FIG. 4 shows a section view of a light source and of a shadow sensor of the system according to another embodiment of the invention, in which the Snell's law is applied.

The refraction phenomenon transforms a perfectly regular shadow of the mask 102 into an irregular shadow. This is due to a layer of glass of the mask 102 which is traversed by the light prior to reading by the imager 104, as illustrated in FIG. 4, wherein the air A is over the mask 102 and between the mask 102 and the imager 104. In the FIG. 4, the reference PS indicates the periodic signal or shadow of the ideal case (i.e. refraction), the reference NPS the non-periodic signal or shadow of the real case (i.e. with refraction) and R the region of interest for the position analysis. By assuming a light position, and applying Snell's law, the shape of the shadow may be computed, as is illustrated in FIG. 2.

This shape can be used to compute the shadow position in an iterative process, by starting with an estimate of the position, computing the shadow, slightly changing the position estimate in two opposite directions, and recomputing the shadow for each position change. By correlating the real shadow with these three shadow estimates, the real shadow position can be interpolated. Once said real position is determined, one may preferably recompute the position corresponding to a sensor without refraction prior to apply projective computations to estimate a 6D position.

In a practical environment, the path between a light source 200 and a sensor could be obstructed by the presence of an object or a person. Thus, by having a multitude of light sources 200, and using a temporal multiplexing scheme, in one embodiment it is possible to ensure that at least four light sources 200 are visible within a given temporal window.

For example, if the system has to compute 10 positions per second, and it the acquisition time of a shadow is in the order of 5 ms, in theory one could record the position of 20 lights sources to perform the computation. Thus, if at least four of these 20 are available, then the system can compute the 6D position of the shadow sensor with respect to the light sources.

To record the projection of light sources 200, a shadow sensor 100 may sense several different wavelengths, use a temporal multiplexing scheme, or a combination of sensing several wavelengths and a temporal multiplexing scheme.

Temporal multiplexing allows handling more light sources 200 with simpler and less expensive hardware, particularly where the target on which they can be placed does not move fast (e.g., having a displacement larger than 10% of the desired (x, y, z) precision). However, temporal multiplexing may be less capable depending on the motion of the light sources 200 in-between the shadow acquisition. The 6D computation is based on the target, i.e. the ensemble or constellation of light sources, considered as a rigid body during the computation, which means that the relative positions of the target LEDs are fixed. Thus, a target that moves between each light source shadow acquisition is equivalent to a target where the light source can have a relative and unknown displacement, thereby resulting in a poor 6D position computation.

To solve the motion issues, the shadow acquisition is performed as fast as possible. In addition, by temporally tracking the position of each light source 200 individually, and knowing when the measurement took place, the position of each light source over time can be interpolated.

Thus, using these interpolated values, the 6D position of the target may be computed by taking the position of each light source at a given time.

The position of the light source is interpolated in a 3D space when using a double shadow sensor (or stereo shadow sensor), or in a 2D projection space when using a single shadow sensor. The simplest interpolation model assumes that the light source travels at constant speed. More elaborate models use a constant acceleration, or a continuous acceleration assumption (without jumps), and can use a Kalmann filter to track the speed and acceleration of each light source over time.

In the temporal multiplexing scheme, the projection corresponding to each light source should be known. Thus, in one embodiment, communication means as a radiofrequency link can be used to send an ID of the light sources 200 and to sync their light emission with the recording of the shadow by the shadow sensor 100.

To avoid using radio frequency, other embodiments may use an additional photodiode which is sampled at higher temporal frequency than the recording of the shadow (for example at 10 times higher temporal frequency). If a filter is used in a shadow sensor 100, then the photodiode may be placed behind the filter of the shadow sensor 100, next to the imager 104.

This additional photodiode serves two purposes: it is used to sync the recording of the shadow with the light emission and is used to identify which light source 200 is emitting light. This can be done, for example, by varying the emission delay in-between the light sources, such that by measuring the time interval between two or more light emissions, it is possible to determine when each light source 200 is emitting light. Therefore, it is also possible to determine the projection corresponding to each light source.

One advantage to using an additional photodiode instead of a radio frequency link is that the additional photodiode is more cost effective. Moreover, it is possible to measure the visibility of each light source 200 to estimate a very approximate position in a context with a large measurement volume and a lot of light source 200, e.g. more than 10 light sources 200.

Alternatively, a shadow sensor in the temporal multiplexing scheme could be used without the additional photodiode. This embodiment is cheaper as use the shadow sensor 100 itself as a photodiode. In one preferred embodiment, the clocks of the plurality of light sources 200 are sync with the clock of the shadow sensor 100, and then the shadow sensor is used as described above to compute the 6D position. Then the process is repeated whenever the clocks of the plurality of light sources 200 and the clock of the shadow sensor 100 might be out of sync.

In such embodiment, the shadow sensor effectively operates as a single photodiode, i.e. it is arranged for taking images at a high framerate and summing the captured pixels to generate a single value, that can be considered as a photodiode reading. The single value is proportional to the value that would have been obtained using the additional photodiode. Since the summation process reduces the noise, the shadow sensor can be operated at a framerate higher than what would be typically reasonable for position computation. Therefore, the same method described above with respect to the photodiode may be used with the single value generated by the shadow sensor 100.

Regarding the sensing of several wavelengths, as described in the WO 2012/007561, a shadow sensor 100 can simultaneously record the projection of several light sources by using light sources 200 with distinct spectra, and dividing the sensor 100 into zones with distinct frequency responses. The zones can be large zones covering several periods of the mask 102, or small zones, for example, using a filter having the size of a single pixel. In the latter case, the filters are placed on the pixels of the imager 102, whereas in the former case, the filter can be placed either near the mask 102, near the imager 104, or anywhere in-between.

The filters do not need to be perfectly matched to the light source spectra; rather, it suffices that the influence of each light source 200 for each filtered response can be recovered. In other words, if a squared matrix of responses, where each line represents the response to each light source and each column represents the response for each filter, is invertible, then it is possible to distinguish the influence of each light source 200. To ensure a good resilience to noise, this matrix has, in some embodiments, a condition number below 100, and in other embodiments, below 10. The signal to noise ratio can be further enhanced by having light sources with sharp spectral emissions, and filters with sharp spectral responses at the same frequency as the light sources 200.

In one preferred embodiment, the system according to the invention comprises a LEDs' assembly as the plurality of the light sources 200, a set of shadow sensors, and a processor arranged so as to compute the position of each shadow sensor 100 with respect to the LED assembly. In one preferred embodiment, the LED assembly comprises height or more LEDs, and preferably not all on the same plane.

Figure 5A:
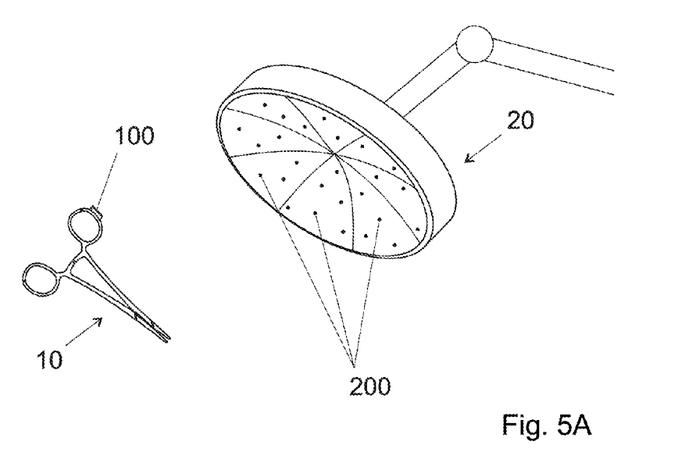
FIG. 5A shows an example of a system according to the invention, comprising a surgical lamp comprising a plurality of light sources and a surgical tool comprising a shadow sensor.

FIG. 5A shows an example of a system according to the invention, comprising a surgical lamp 20 comprising a plurality of light sources 200 and a surgical tool 10 comprising a shadow sensor 100. In a preferred embodiment, the relative position of some, preferably all the light sources 200 is known. In the illustrated embodiment, all the light sources 200 are integrated in a surgical lamp 20. In the illustrated embodiment, the light sources 200 are connected, and if a radio link is used to sync the shadow sensor 100, then only one radio emitter is needed for the light sources 200.

In one preferred embodiment, the light sources are emitting light not belonging to the visible spectrum, e.g. infrared light, so as to not interfere with the light of the surgical lamp 20.

In one preferred embodiment, to ease the computation, among all the light sources 200, four can be placed on the same plane: in such a case a linear method can be used to compute the first 6D position after waking up the system according to the invention.

Figure 5B:
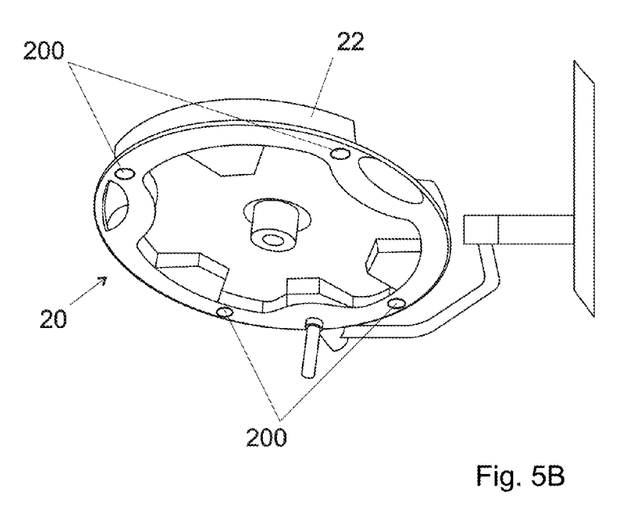
FIG. 5B shows an example of another surgical lamp comprising a plurality of light sources according to the invention.

FIG. 5B shows an example of another surgical lamp 20 comprising a plurality of light sources 200 according to the invention. In this embodiment, the light sources 200 are integrated in the frame 22 of the lamp 20, e.g. a highly rigid frame holds the LEDs internally.

In another preferred embodiment, the system comprises a set of at least two light source modules 30. An example of light source module 30 is visible in FIG. 6. It comprises:
- a light source 200, e.g. a LED;
- communication means 400 for communicating with other light source modules, e.g. a radio link;
- a clock;
- fixation means 600 for fixing the module 30 on a support, e.g. a wall, a ceiling, a furniture. For example, the fixation means comprise a magnet, a tape, etc.

Figure 6:
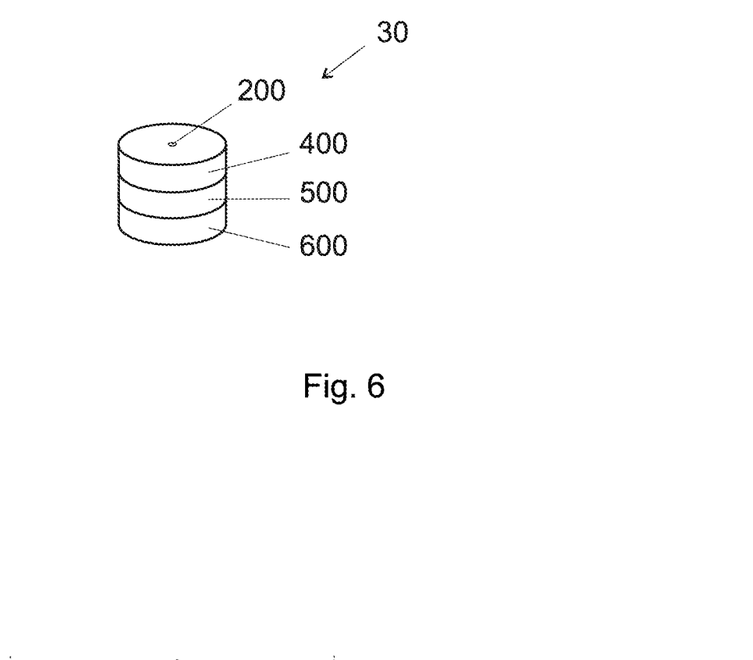
FIG. 6 shows a perspective view of a light source module according to one embodiment of the invention.

The positioning system according to this embodiment can be deployed rapidly. This embodiment allows, for example, to install a positioning system in a new room by attaching at least two modules, preferably a multitude of these modules 30, at fixed locations in a volume, e.g. a room (on walls, ceiling or fixed furniture). The volume is not necessarily closed. The fixation means 600 allow the modules 30 to be easily placed at arbitrary positions within a volume.

In one embodiment, each module 30 comprises a light source 200 as a LED 200, a clock and radio frequency link (emission and reception) 400 and a battery 500. In one embodiment one module 30 of the set acts as master, the others as slave. In another embodiment, only the module 30 acting as a master comprises a radio frequency link, and a wired network connects it to any other modules, which then do not require a battery, nor a radio link.

A calibration phase is needed prior to be able to track any number of shadow sensors 100 in the room. Another advantage is the ability to correct for blind spots by adding additional modules 30 and repeating the calibration phase. A "blind spot" in this context is a (5D) position where the shadow sensor 100 is unable to record a sufficient amount of LEDs projections, and is thus unable to compute its position.

In a discovery phase, every module 30 announces itself so as to construct a list of all the modules 30 that are present in the volume.

In an initialisation phase, the clocks of all the modules 30 are synced and a flash timing is assigned to each module 30 by a master, which can be one of the modules 30. Then, each light source 200 is flashing according to its scheduled timing.

Then follows a calibration phase: a shadow sensor 100 is placed in the volume, e.g. in the room. It makes a reading of all the light sources 200 of the modules 300 while being in a fixed (6D) position.

The shadow sensor 100 is displaced, and a new reading is performed. For each reading, the (x, y) projection of the light sources 200 on the sensor 100 is recorded. Optionally, a scale or z value can be recorded, and the reliability of the reading (for example the contrast of the shadow) may be recorded as well.

If a light source 200 is not visible, the reading is marked as missing, and if reliability is recorded, it is set to 0. The process of displacing the sensor and reading the light sources 200 is repeated until the complete 3D constellation of the light sources 200 is computed. More reading can then be added to improve the results, as will be discussed.

A the end of the calibration phase, the 3D location of every light sources 200 is know and recorded, the 6D pose of the shadow sensor 100 at each reading known as well, and a partial visibility map for every light source 200 at each reading location can be read as well. In this context, the "visibility map" is a map indicating the reliability of each light source 200 reading at every location in the room. The visibility depends on the 3D location and orientation of the shadow sensor 100, but a rotation of the sensor around its optical axis does not affect the visibility of the LED: therefore, the visibility map is a 5 dimensional map, and not a 6 dimensional map.

From this visibility map, the scheduling of the light sources 200 can be reordered in such a way that light sources 200 that are close together emit within a short period of time. For example, by setting the exposure time to 4 milliseconds, and waiting 2 milliseconds in-between captures, the whole acquisition process will take 22 milliseconds for a constellation comprising four light sources (in this scenario, the image of the shadow may be stored in a temporary memory buffer, so as to start the recording of the next light source before having computed the shadow position).

If a set of light sources 200 are on the right side of a room, and another set on the left side of the room, then the left light sources 200 are flashed (one after the other), followed by the right light sources 200, followed by the left light sources 200, etc. In this way, a shadow sensor 100 placed on the left side of the room is able to record a set of projection in a short amount of time; which is a condition for having a good precision if the shadow sensor 100 is in motion.

If this rescheduling is not done, then in the example above, the time to get enough light sources reading would be made longer because some light sources from the right side of the room would flash inbetween the light sources of the left side of the room. By assuming that the light sources on the right are not visible, or barely visible on the left of the room, they cannot be used to compute the shadow sensor position.

Once these steps are completed, the system is ready for use, i.e. any shadow sensor 100 in the volume can compute its position over time, and send the result, e.g. via an RF link to a base station.

As an option, the sensor 100 comprises a processor 108 (visible on FIG. 8) so as to perform a (x, y) reading (and optionally Z and visibility reading) and send this information to an external processor 800 which will compute the (6D) position of the shadow sensor 100. In another embodiment, the processor 108 of the shadow sensor perform the (6D) position of the shadow sensor 100 as well.

On very large volumes, for examples volumes covering a whole room or a whole storehouse, the exposure schedule of some the light sources 200 can be overlapped, provided these light sources 200 are not visible from the same location. In other words, there must be no location (in 5D) where any two light sources 200 with overlapping schedule have a visibility value above a very small threshold (the threshold can be even put to 0). In this context, the expression 'overlapping threshold' indicates that when one of the light sources 200 is turned on, then the second light source 200 is turned on before the first light source 200 is turned off.

In practice, it is preferable to slightly differentiate the trigger schedule of every light source 200, so that when recording the signal with a photodiode with a high sampling rate, it is possible to know which of the light sources 200 with overlapping schedule is visible.

This is useful in situations where the shadow sensor 100 does not (yet) know it's location: by measuring the visibility of some the of light sources 200, and using the visibility map, it can compute a rough estimate of its position, then adjust the exposure schedule of the shadow sensor 100 to record shadows from light sources 200 in the sensor vicinity in order to precisely measure its location.

The applicant discovered surprisingly that recording the position of the shadow of the light source 200 with a sensor 100 that does not move, is equivalent to detecting a set of corresponding feature points in a multiple view scenario using a pinhole camera. It is therefore possible to compute the sensor position when having recorded the light sources 200 projections from several locations.

The correspondence of the feature points is given by the ID of the light source 200 which was flashing when the shadow was recorded, the coordinate of the point is given by the coordinates (x, y) of the shadow, and the set of features in the image or "view" of the pinhole camera is the set of coordinates recorded from a given (fixed) location of the shadow sensor 100.

It is possible to use the theory of multiple view geometry. The shadow sensor can be considered as being a pinhole camera, because the geometric configuration of the imager 104 in the shadow sensor 100 is known, and the focal length f can be considered as the distance between the mask 102 and the imager 104.

The following table summarizes how many "views" and the minimal number of points per image that must be recorded to solve the joint problem of sensor pose and LED pose estimation. The noun "views" indicates all the recordings taken from a shadow sensor in a given (fixed) position. In other words, the following table indicates the constraints on the minimum number of visible points P (preferably not coplanar) to retrieve the complete system geometrical configuration up to a scale factor with a single shadow sensor:

| Number of views N | Number of points P |
| --- | --- |
| 2 | 8 |
| 3 | 7 |
| 4 | 6 |

There is one additional constraint linked to the fundamental scale indetermination of the method according to the invention: in a preferred embodiment using a single shadow sensor during the calibration process, the relative position of at least two light sources 200 in the set under measure is known.

Figure 7:
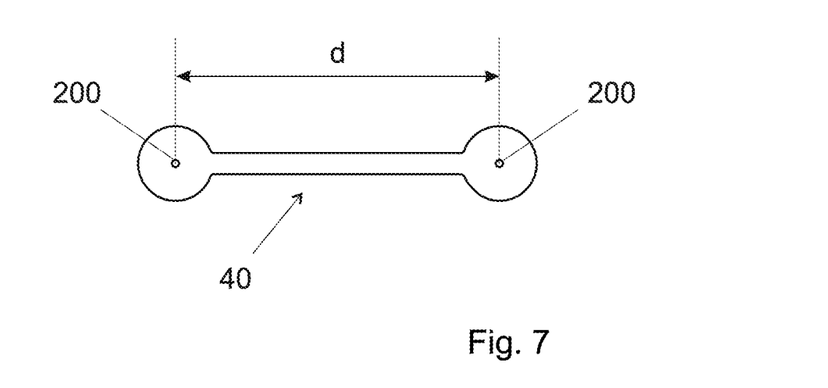
FIG. 7 shows a top view of an assembly comprising two light sources with known relative position according to one embodiment of the invention.

FIG. 7 shows a top view of an assembly 40 comprising two light sources modules 30 with known relative position according to one embodiment of the invention. The relative position d is therefore known. The assembly 40 can be used to alleviate the scale indetermination in the calibration phase.

In another embodiment, the distance between two particular light sources 200 of the system can be set by software.

The scale determination is done by applying the complete estimation process, measuring the distance between the two light sources with known distance d according to the coordinates in this first version of the solution, and multiplying every spatial coordinate of every location (light source and sensor) by a common factor such that the distance between the two light sources 200 with known distance d becomes the correct distance (the orientation coordinates remain unchanged).

The dual solution to using the assembly 40 to solve the scale indetermination problem is by using a stereo shadow sensor whose baseline is known. By knowing the baseline distance between the two sensors 100, the stereo sensor can estimate the 3D position of each light source 200 in space without having an overall scale indetermination. When a stereo shadow sensor is available, this solution is preferred to the one using a single shadow sensor, as this solution requires a lower number of light sources simultaneously visible by the shadow sensor. Moreover, this solution is more precise in terms of S/N issues.

To compute the solution, i.e. the pose of every light source 200 and set of sensor 100 fixed locations, a matrix of visibility can be built. In one preferred embodiment, this matrix comprises on the columns the light sources 200 ID, and on the rows the (fixed) location of the sensors. In a preferred embodiment, the matrix is binary, and for each location it defines whether a light source 200 is visible or not. From there, one has to find the combination of location of light sources 200 and sensor 100 that fulfils the requirement of the previous table.

For example, one can find two locations where there are 8 LEDs (or more) that are visible simultaneously (in other words, two lines of the matrix which share a "true" on at least height columns). From there, the pose of the sensor location and LEDs can be derived.

Once a first set of pose is derived then:
to compute the location of an additional light source 200, it suffices that it appears in two locations with known pose,
to compute a new location of the sensor 100, it suffices that it has four light source 200 projections with known location that are visible.

By iterating on these criteria, it is possible to reconstruct the whole light sources' constellation along with every sensor location. If this is not possible, i.e. if the problem has no solution, then the user of the system is asked to either add some more modules 30 in the volume, or take more recordings.

To effectively solve the location problem given a number of visible light sources 200 and a number of sensor location, it is possible to apply the algorithm described in chapter 18 of the document R. Hartley and A. Zisserman, *Multiple view geometry in computer vision*, second edition, Cambridge University Press, using projective factorization followed by bundle adjustment. In fact according to the invention the shadow sensor is a pinhole or projective camera with known calibration parameters. In one preferred embodiment, the shadow sensor is calibrated at some point in time, prior to using it in 6D computations.

There are applications that require rendering the result of the traking of the sensors in a CAD design. To register the system with a cad design, one can define in the CAD design where some particular light sources 200 should appear in the CAD, and perform a bundle adjustment to align the coordinate system of the light sources 200 constellation with the coordinate system of the CAD design.

For example, the exact position of some of the light sources 200 can be known in the CAD reference frame; this allows to register the CAD coordinate frame with the sensor coordinate frame.

A more practical approach is to set the constraint that (at least) three light sources 200 are on a surface—for example a wall—in the CAD system, (at least) two additional light sources 200 is on a second (different) surface, and yet another light source 200 is on a third surface different from the two former surface; in this context, it is also possible to align the CAD and sensor corner frames.

If a stereo shadow sensor whose baseline is known is used, the bundle adjustment that follows is then simplified because the computation can be done in 3D instead of being done in projective space. To calibrate such a system, it must record a position with at least three light sources 200 visible in the field of view. Then, to further compute the position of each light source 200, any following recordings must have at least three light sources 200 with known position and at least one light source 200 with unknown position, whose 3D position is computed using said recording. Once every LED location is computed, the system can work with a single shadow sensor, provided that at least four light sources 200 are visible in the field of view, or with a stereo shadow sensor provided that at least three light sources 200 are visible in the field of view.

Figure 8:
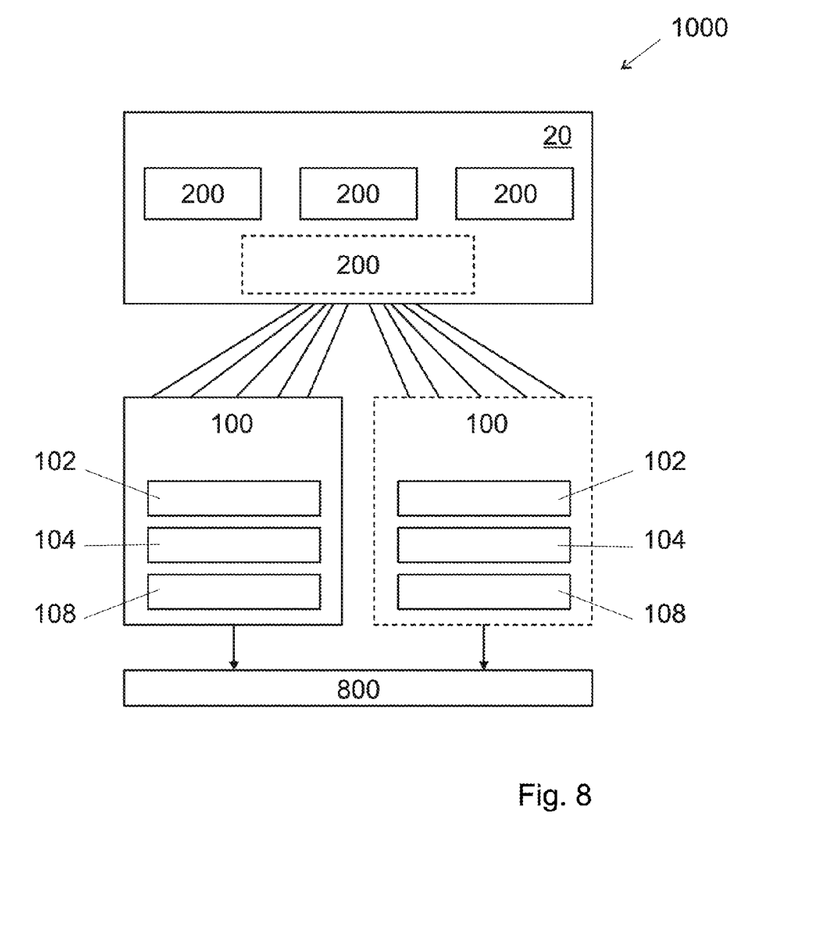
FIG. 8 shows a block diagram of a positioning system according to one embodiment of the invention.

These possibilities are illustrated in the block diagram of FIG. 8, representing the positioning system 1000 according to one embodiment of the invention. If two shadow sensors 100 are used, then at least three light sources 200 are necessary. If one shadow sensor 100 is used, then at least four light sources 200 are necessary.

In one preferred embodiment, in the calibration phase, where the location of every light source is computed, the number of light sources that must be visible simultaneously is larger than when using the system to determine the position of the shadow sensor with respect to the constellation of the light sources.

This invention discloses a system that computes a six-dimensional position of a sensor with respect to a constellation of light sources. While this six dimensional computation is performed inside to the sensors, or by an external computation facility, the information that is needed, recorded or transmitted may not be six dimensional. For example, some application may only require to know the 2D (or 3D) position of a sensor inside a room. In the latter case, the six dimensional position of the sensor is computed inside to the sensors, or by an external computation facility, from which the 2D (or 3D) position is extracted and communicated to the user (or to the system that needs this information).

There are however situations where the six dimensional computation of the position is not necessary. These situations occur when there are some constraints on the orientation of the sensor. It is the case when the light sources used in the computation are all on one plane, and where the shadow sensor mask is parallel to this plane. If the distance between the shadow mask and the plane is fixed, then the computation is a 2D translation+1D rotation computation, i.e. a 3D computation. If this distance is varying, then the computation can be performed in 4D, i.e. a 3D translation+1D rotation. In both situation, the computation can be performed using first a linear affine transformation, followed by a non-linear bundle adjustment. It uses conventional geometry and avoids the projective geometry considerations.

For example, if the sensor is fixed on a shopping cart, and the light sources are placed on the ceiling of the store, the internal computation will be performed by estimating the 2D position+1D orientation of the shopping cart, while probably transmitting only the 2D position of the shopping cart to the positioning system. In this example, the distance between the plane containing the light sources, i.e. the ceiling, is fixed with respect to the shopping cart which rolls on the floor (it assumes the ceiling is at constant height and parallel to the floor).

Another example of such a system is when the sensor is fixed on a pallet truck. If the sensor is placed on the part of the truck that goes up and down, then it will be using a 3D position estimation+1D orientation internally to perform the computation.

REFERENCE SIGNS USED IN THE FIGURES

1 Recording step
2 6D position estimate computing the step
3 Re-projecting step
4 Error computing step
5 Error checking step
6 Iteration numbers checking step
7 6D position estimate correcting step
8 No position available step
9 6D position estimate step
10 Surgical tool
20 Surgical lamp
22 Frame of the surgical lamp
40 Assembly comprising two shadow sensors
100 Shadow sensor
102 Mask
104 Imager
108 Processor of the shadow sensor
200 Light source
300 Object point
302 Pin-hole camera
304 Image plane (imager)
306 Pinhole
400 Communication means
500 Battery
600 Fixation means
800 External processor
1000 System
d Distance
f Focal length
t Thickness
x Bi-dimensional position
A Air
PS Periodic signal (ideal case, without refraction)
NPS Non periodic signal (real case, with refraction)
R Range of interest for position analysis

The invention claimed is:

1. A six dimensional (6D) positioning system, comprising:
   a surgical tool;
   a surgical lamp;
   a plurality of light sources positioned at fixed relative locations in or on the surgical lamp;
   at least one shadow sensor placed on the surgical tool and configured to sense shadows cast on the shadow sensor by light emitted from the light sources, said shadow sensor comprising an imager; and
   a processor; wherein:
   the maximum distance between any of said light sources is larger than fifty times a width or a height of said imager; and
   the processor is configured to:
   sync a shadow sensing with a pulsing of the light sources;
   distinguish between the sensed shadows from each of the light sources;

determine two dimensional positions corresponding to each of the light sources based on the sensed shadows; and compute a six dimensional (6D) position of the at least one shadow sensor with respect to the light sources based on the determined 2D positions.

2. The positioning system according to claim 1, wherein the system comprises several shadow sensors and wherein the processor is configured to compute the 6D position of said several shadow sensors.

3. The positioning system according to claim 1, wherein the number of light sources is equal or higher than three, the system comprises an assembly comprising two shadow sensors with known relative position and wherein the processor is configured to compute the 6D position of said assembly.

4. The positioning system according to claim 1, wherein the shadow sensor comprises a mask, the mask having repetitive elements and a distinctive element, and wherein as light from the light sources passes through the mask, a shadow of the mask is cast on the imager.

5. The positioning system according to claim 1, wherein the processor is configured to distinguish between the sensed light from each of the light sources based at least in part on temporal modulation of the light sources.

6. The positioning system according to claim 1, wherein each shadow sensor further comprises a photodiode for syncing the shadow sensing with the pulsing of the light sources and/or for identifying which light source is emitting light.

7. The positioning system according to claim 1, wherein the 6D position of the shadow sensor is computed as if the shadow sensor were a pinhole camera so as to use projective geometry computations.

8. The positioning system according to claim 1, wherein the light sources are connected and wherein a radio link is used to sync the shadow sensor.

9. A six dimensional (6D) positioning system, comprising:
a set of at least two light source modules, each light source module comprising:
a light source;
communication means for communicating with other light source modules;
a clock;
fixation means for fixing the module on a support
at least one shadow sensor configured to sense shadows cast on the shadow sensor by light emitted from the light sources of the light source modules, said shadow sensor comprising an imager; and
a processor; wherein:
the maximum distance between the light sources is larger than fifty times a width or a height of said imager, and the processor is configured to:
sync a shadow sensing with a pulsing of the light sources;
distinguish between the sensed shadows from each of the light sources;
determine two dimensional positions corresponding to each of the light sources based on the sensed shadows; and
compute a six dimensional (6D) position of the at least one shadow sensor with respect to the light sources based on the determined 2D positions.

10. The positioning system according to claim 9, a light source module comprising a battery and RF communication means, the system comprising a wired network connecting said light source module with at least one other light source module.

11. The positioning system according to claim 9, each light source module comprising a battery and the communication means being RF communication means.

12. A method for estimating a six dimensional (6D) position, of a shadow sensor with respect to a plurality of light sources, the shadow sensor being configured to sense shadows cast on the shadow sensor by light emitted from the light sources, said shadow sensor comprising an imager, the maximum distance between any of said light sources being larger than fifty times a width or a height of said imager, the method comprising:
sync a shadow sensing with a pulsing of the light sources;
distinguish between the sensed shadows from each of the light sources;
determine two dimensional (2D) positions corresponding to each of the light sources based on the sensed shadows;
compute a 6D position of the at least one shadow sensor with respect to the light sources based on the determined 2D positions;
sense shadows cast on the shadow sensor by light emitted from the light sources, wherein at least two light sources are at a fixed position with respect to each other;
record a projection of at least six points from a fixed location, each point corresponding to the three dimensional (3D) position in space of a light source, a projection of a point being recorded as the two dimensional (2D) position of the sensed shadow cast by said light source on said shadow sensor;
repeat said recording and computing steps from a different fixed location, so as to obtain N recordings comprising each the projection of a set of the same P light sources, N and P being integer numbers satisfying a predetermined constraint;
compute the three dimensional (3D) relative position of every light source within a common reference frame, said position being defined up to a scale factor; and
scale every computed three dimensional (3D) relative position so that the computed three dimensional (3D) relative position of said at least two light sources matches said known fixed position.

13. The method of claim 12, further comprising the following steps:
sense shadows cast on an assembly comprising at least two shadow sensors with known relative positions, by light emitted from the light sources,
record a projection of at least three points from a fixed location, each point corresponding to the (3D) position in space of a light source, a projection of a point being recorded as the two dimensional (2D) positions of the sensed shadows cast by said light source on each shadow sensor of said assembly;
compute the three dimensional position of each point with respect to said fixed location;
repeat said recording and computing steps from a different fixed location, so as to obtain M recordings comprising each the projection of a set of the same Q light sources, M and Q being integer numbers satisfying a predetermined constraint;
estimate the three dimensional (3D) relative position of every light source within a common reference frame.

* * * * *